United States Patent [19]

Elben et al.

[11] Patent Number: 4,792,554

[45] Date of Patent: Dec. 20, 1988

[54] PYRIDINE COMPOUNDS, PHARACEUTICAL COMPOSITIONS, THEIR USE IN ALLERGY THERAPY

[75] Inventors: Ulrich Elben, Wiesbaden; Hiristo Anagnostopulos, Taunusstein; Robert R. Bartlett, Darmstadt, all of Fed. Rep. of Germany

[73] Assignee: Hoechst Aktiengesellschaft, Frankfurt am Main, Fed. Rep. of Germany

[21] Appl. No.: 933,532

[22] Filed: Nov. 21, 1986

[30] Foreign Application Priority Data

Nov. 23, 1985 [DE] Fed. Rep. of Germany ....... 3541428

[51] Int. Cl.$^4$ ................ A61K 31/495; A61K 31/44; C07D 295/12
[52] U.S. Cl. .................... 514/255; 514/318; 544/360; 546/193; 546/194
[58] Field of Search ................ 544/360; 514/255, 318; 546/193, 194

[56] References Cited

U.S. PATENT DOCUMENTS 4,115,396 9/1978 Ursprung ........................... 544/360
4,289,765 9/1981 Greve et al. ........................... 544/3

FOREIGN PATENT DOCUMENTS 0135087 3/1985 European Pat. Off.
2334401 1/1975 Fed. Rep. of Germany.
2900504 7/1980 Fed. Rep. of Germany.

OTHER PUBLICATIONS

Fisons Pharmaceuticals Ltd. CA 67-100002d (1967) eq. to UK 1144905.
Pirisino et al., CA 99-166C (1983).

*Primary Examiner*—Donald G. Daus
*Assistant Examiner*—C. Shen
*Attorney, Agent, or Firm*—Finnegan, Henderson, Farabow, Garrett, & Dunner

[57] ABSTRACT

A pyridine compound of the formula I in which $R^1$ and $R^2$ independently of each other represent hydrogen or alkyl having from 1 to 4 carbon atoms, $R^3$ represents hydrogen or alkyl having up to 2 carbon atoms and A represents alkylene having 2 to 4 carbon atoms, n is 0 or 1, Z is a group of the formula Za, Zb or Zc (Za)  (Zb)  (Zc)

in which either $R^4$ is hydrogen and $R^5$ is phenyl or cinnamyl or $R^4$, $R^5$, $R^7$ and $R^8$ independently of each other are pyridyl, phenyl or phenyl which is substituted by up to 2 equal or different substituents from the group halogen and alkoxy having up to 2 carbon atoms, $R^6$ is hydrogen or hydroxy and X is hydrogen, a cyano, amino or nitro group or the group —CO—$R^9$, in whcih $R^9$ is hydroxy or alkoxy having from 1 to 4 carbon atoms, and the physiologically tolerable salts of these compounds. The invention also relates to a process for the manufacture of such compounds and to their use in pharmaceutical compositions.

19 Claims, No Drawings

PYRIDINE COMPOUNDS, PHARACEUTICAL COMPOSITIONS, THEIR USE IN ALLERGY THERAPY

An allergic reaction which is triggered in the human body by allergens and is of what is called the "immediate type" becomes manifest only a few seconds after contact with the allergen in the form of, for example, pruritus, (dermatitis), sneezing (rhinitis) or coughing and shortness of breath (asthma). These symptoms are brought about by the explosive release, during the antigen-antibody reaction, from the tissue mast cells of mediators which have a spasmogenic activity, such as histamine, bradykinin, PAF (platelet-activating factor), leukotrienes ($C_4$, $D_4$, $E_4$), prostaglandins ($D_2$) and others, the anaphylactic antibodies belonging to immunoglobulin class E (IgE). Whereas the first three of the said mediators are present in the mast cell in stored form, the excessive formation of leukotrienes and prostaglandins from arachidonic acid in the cell membrane takes place only during the course of the immediate anaphylactic reaction.

Accordingly, for an allergy therapy to be promising it must aim at effectively interrupting the self-destructive process, which takes place like a cascade, of the IgE-mediated immune reaction at at least one of several possible points of attack. In principle two therapeutic approaches appear suitable for this, namely causal and symptomatic treatment. Causal therapy comprises avoidance of exposure to the particular allergen, or specific hyposensitization of the person with the allergy. However, clinical experience has shown that no more than 15% of all the patients suffering from exogenic allergic disorders can be treated in this way.

Hence allergy therapy primarily takes the form of symptomatic treatment with medicaments which either prevent the release of spasmogenic mediators or suppress their interaction with their specific receptors. A dominating role is played in this by the antihistamines known as $H_1$-receptor antagonists. However, since the body is equipped with $H_1$ receptors not only in the periphery, such as, for example, in the bronchial system, but also in the central nervous system, antihistamines whose intervention is nonselective bring about, via simultaneous blockade of the central receptors, pronounced sedation (drowsiness) which is a serious side effect which is very detrimental to the daily life of the patient. The compound ketotifen is a classical example of this.

Consequently, the best therapeutic prospects for allergic conditioned disorders of the IgE-mediated immediate type are offered by those drugs which effectively inhibit the release of histamine and the other mediators of allergy mentioned in the introduction, block only the peripheral $H_1$ receptors and, at the same time, exert their action very rapidly even after oral administration.

German Offenlegungsschrift No. 2,900,504 (=U.S. Pat. No. 4,289,765) discloses pyridine compounds which have bronchospasmolytic activity and, although they have antihistaminic activity, they have, as is shown by comparison tests in the pharmacological experiment part of the present description, no action against the IgE-mediated release of mediators of allergy from the mast cells and, accordingly, they cannot be used for the therapy of exogenic allergic disorders.

While the substance CHROMOGLICIC ACID which is described in British Pat. No. 1,144,905 as stabilizing mast cells can be administered by inhalation, it cannot be administered orally and, in particular, it can be administered only for prophylaxis. The tricyclic compound KETOTIFEN, and the benzimidazolone derivative OXATOMIDE, additionally have antagonistic properties for histamine and leukotrienes, but they cannot be administered by inhalation. Since OXATOMIDE does not exert its action until several days have passed its use has to be restricted mainly to the treatment of chronic allergy cases. Furthermore, both products cause pronounced sedation as an undesired side effect in animals and humans. In contrast, the butanol derivative TERFENADINE and the benzimidazole compound ASTEMIZOLE are said to have no sedative side effect. However, because of insolubility in water, neither product can be administered by inhalation, and both result, as do other antihistamines, in an undesired weight gain on long-term therapy.

It is true of all the active compounds mentioned above that there exist no injection solutions which would allow, in acute situations, rapid intervention by parenteral administration.

It has now been found, surprisingly, that the introduction into the 4-position of 3-substituted 2,6-dialkyl-pyridines, and their 1-oxides, of certain alkylamino groups carrying basic groups results in new compounds which, by reason of their valuable pharmacological properties, are very suitable for the treatment of allergically conditioned disorders of the IgE-mediated immediate type. They exhibit a pronounced ihibitory action on the spasmogens histamine, bradykinin, platelet activating factor (PAF) and the leukotrienes, effectively inhibit, via their protective effect on mast cells, the release of these allergy mediators, have no sedative side effect and can be administered parenterally, by inhalation or orally, it being guaranteed that the onset of action is rapid. Consequently, they have a hitherto unknown optimal profile of action, and hence make possible a far more effective therapy of allergic discrders than the products of the state of the art, which have only part of the activities in the ideal spectrum of actions described above.

Furthermore, the compounds according to the invention are also suitable as starting materials for the synthesis of other valuable drugs.

Accordingly, the present invention relates to new pyridine compounds having basic substituents, including the relevant salts, to a process for their preparation and to their use in medicaments, in particular in those which are indicated for atopic respiratory tract disorders, such as allergic rhinitis, allergic asthma and anaphylactic shock, as well as for allergic dermatitis and allergic conjunctivitis.

Thus the invention relates to the pyridine derivatives of the formula I (see patent claim 1) in which $R^1$ and $R^2$, independently of one another, represent hydrogen or alkyl having 1 to 4 carbon atoms, $R^3$ denotes hydrogen or alkyl having 1 or 2 carbon atoms, and A denotes straight-chain or branched alkylene having 2 to 4 carbon atoms, n has the value 0 or 1, Z represents a group of the formula Za, Zb or Zc (see patent claim 1), either $R^4$ denoting hydrogen and $R^5$ denoting phenyl or cinnamyl or $R^4$, $R^5$, $R^7$ and independently of one another, each denoting pyridyl or phenyl, the phenyl optionally carrying one or two identical or different substituents from the group comprising halogen and alkoxy having 1 or 2 carbon atoms, $R^6$ denoting hydrogen or hydroxyl, and X denoting hydrogen, the cyano, amino or nitro group or the radical —CO—$R^9$, in which $R^9$ represents hydroxyl or alkoxy having 1 to 4 carbon atoms, and to the physiologically tolerated salts of these compounds.

The compounds of the formula I and their salts which are preferred are those in which the radicals $R^1$ and $R^2$ together contain not more than 6 and, in particular, not more than 2 carbon atoms, and/or the halogen, where present, on the phenyl rings represents fluorine, chlorine or bromine, and/or the alkylene bridge A denotes ethylene. Among these compounds, particular attention is drawn to those, and their salts, in which $R^1$ and $R^2$ each denote methyl, $R^3$ denotes hydrogen, A denotes ethylene, Z the group of the formula Za or Zb and X denotes the cyano or nitro group. In general, and especially among these, those compounds which are worthy of special interest are those and their salts in which Z represents the group of the formula Za, and $R^4$ and $R^5$ have the meaning of phenyl which is optionally substituted by up to two identical or different halogen atoms. The compounds which particularly belong in this preferred group are 3-nitro-and 3-cyano-2,6-dimethyl-4[(2-{4-diphenylmethyl-1-piperazinyl}ethyl)amino]pyridine and their 1-oxides and the salts of these compounds.

The invention furthermore relates to a process for the preparation of the pyridine compounds of the formula I and of their physiologically tolerated salts, which comprises (a) reaction of a compound of the formula II (see formula sheet) with a cyclic amine of the formula III

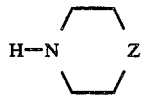

the abovementioned meanings applying to $R^1$ to $R^3$, n, X, A and Z with $R^4$ to $R^8$ and Y representing a leaving group, such as halogen, preferably chlorine, bromine or iodine, a sulfonic ester or phosphoric ester group, or (b) reaction of a compound of the formula IV (see formula sheet), in which $R^1$ to $R^3$, n, X and A have the above-mentioned meanings, with a compound of the formula V

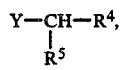

in which $R^4$, $R^5$ and Y have the abovementioned meanings, to give a compound of the formula I having the structural element Za, or (c) reaction of a compound of the formula VI (see formula sheet), in which $R^1$ to $R^3$, n and X have the above-mentioned meanings, with a compound of the formula (VII)

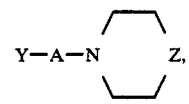

Y, A and Z with $R^4$ to $R^8$ having the abovementioned meanings, or (d) reaction of a compound of the formula VIII (see formula sheet) with an amine of the formula IX

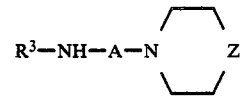

to $R^3$, n, X, A and Z with $R^4$ to $R^8$ having the meanings defined above, and Hal representing a halogen atom, and isolation of the product obtained as in process variant (a), (b), (c) or (d), it also being possible to prepare (e) a compound of the formula I in which X represents the amino group, which is preferred, by reduction of a 3-nitro compound of the formula I obtained as in (a), (b), (c) or (d), or (f) it also being possible to prepare a compound of the formulaI in which X denotes the carboxyl group by hydrolysis of a 3-carboxylic ester of the formula I obtained as in (a), (b), (c) or (d), or (g) it also being possible to prepare a compound of the formula I having the structural feature Zc by dehydration of a compound of the formula I which has the structural element Zb in which $R^6$ has the meaning of hydroxyl, and which has been obtained as in (a) (b), (c) or (d), the compounds of the formula I being either isolated in free form or converted with suitable acids or, in the case where X represents a carboxyl group, also with suitable bases into physiologically tolerated salts.

Suitable for the preparation of acid addition salts from the compounds of the formula I are, for example, mineral acids such as sulfuric or phosphoric acid or hydrohalic acids, in particular hydrochloric acid, and organic acids such as monobasic to tribasic carboxylic acids, for example acetic, lactic, maleic, fumaric, oxalic, tartaric, citric or gluconic acid, or other physiologically tolerated acids, such as sulfonic acids, for example p-toluenesulfonic, methanesulfonic, trifluoromethylsulfonic and cyclohexylamidosulfonic acid.

The compounds of the formula I in which X represents a carboxyl group can also form with basic reagents, such as hydroxides, alcoholates, carbonates and bicarbonates, stable, water-soluble alkali metal and alkaline earth metal salts.

Most of the starting materials of the formulae II to IX are commercially available, known from the literature or can readily be prepared by methods described in the literature.

Examples of suitable compounds of the formulae II are the 3-substituted 4-[N-(ω-halogenoalkyl)amino]-pyridines which in the 2- and/or 6- position are unsubstituted, monoalkylated or dialkylated and are disclosed in German Offenlegungsschrift No. 2,900,504, such as 4-[N-(2-chloroethyl or 3-chloropropyl)amino]-2,6-dimethyl-3-nitropyridine, -3-cyanopyridine and -3-ethoxycarbonylpyridine and their 2,6-dipropyl derivatives, 4-[N-(2-chloroethyl or 3-chloropropyl)methylamino]-2,6-dimethyl (or -dipropyl)-3-nitropyridine, -3-cyanopyridine and -3-ethoxycarbonylpyridine, as well as the 1-oxides of these pyridine compounds, which can be obtained by N-oxidation by the methods described in German Offenlegungsschrift No. 3,514,073.

Suitable cyclic amines of the formula III are, inter alia, 1-diphenylmethyl-, 1-(4-chloro- or 4,4'-dichloro-diphenylmethyl)-, 1-(4-fluoro- or 4,4'-difluoro-diphenylmethyl)-, 1-(4-chloro-4'-fluoro-diphenylmethyl)-, 1-(phenyl-4(3 or 2)-pyridyl-methyl)-, 1-(4-chlorophenyl-4-pyridyl-methyl)-and 1-(4-methoxy- or 4,4'-dimethoxy-diphenylmethyl)-piperazine and 4-(diphenyl-hydroxymethyl) piperidine (Z=Zb: U.S. Pat. No. 2,804,422) and 4-diphenylmethylene-piperidine (Z=Zc French Pat. No. 2,042,313). For the preparation of the abovementioned piperazines, it is possible to make use of the process described in German Offenlegungsschrift No. 2,714,437 (=British Pat. No. 1,579,365), according to which 1-formylpiperazine is reacted with a compound of the formula V, for example diphenyl-, 4-chlorophenyl(phenyl)-, bis(4-fluorophenyl)-, 4-chlorophenyl-4-fluorophenyl-, phenyl-4-pyridyl- and 4-methoxyphenyl(phenyl)-chloromethane, and then the formyl group is eliminated under alkaline conditions.

The starting compounds of the formula IV can be obtained in the same way by reaction of compounds of the formula II with 1-formylpiperazine and subsequent elimination of the formyl protective group by alkaline hydrolysis.

Examples of suitable pyridine derivatives of the formula VI are the 3-substituted 2,6-unsubstituted, monoalkylated or dialkylated compounds having an amino, methylamino or ethylamino group in the 4-position, and their 1-oxides, which can advantageously be prepared from the corresponding 4-halogen compounds of the formula VIII which are known from the literature (for example German Offenlegungsschrift No. 2,900,504 and patent application No. P 3,514,073) by reaction with ammonia, methylamine or ethylamine.

Most of the cyclic amines of the formulae VII and IX, which are also used as starting materials, are known or can readily be prepared, by literature methods, from the abovementioned amine compounds of the formula III.

The reaction of the particular reactants II to IX in accordance with process variants (a), (b), (c) and (d) is advantageously carried out in a solvent or dispersant whic is inert towards the reactants. Suitable for this purpose are, for example, alcohols such as methanol, ethanol, isopropanol, n-propanol, the various butanols, and mixtures thereof, as well as their mixtures with ethers, such as tetrahydrofuran and dioxane, or hydrocarbons, such as benzene, toluene and xylene, as well as aprotic solvents, such as pyridine, dimethylformamide, dimethylacetamide, dimethyl sulfoxide and hexamethylphosphoric triamide. These condensation reactions are preferably carried out in the presence of at least twice the molar amount of the particular amine used; it is also possible to use equimolar amounts of the two reactants, but it is then advisable to add an acid-binding agent, for example an alkali metal or alkaline earth metal hydroxide or carbonate, or an organic base, suhh as triethylamine, in at least stoichiometric amount. The reaction is generally carried out at temperatures between 0° C. and the boiling point of the particular reaction medium, preferably between 20° and 100° C., it being possible for the reaction time to be as long as several days.

The conversion, where appropriate, of the 3-nitro compounds of the formula I, according to the invention, into the 3-amino compounds of the formula I as in process variant (e) is carried out in a customary manner, for example using metal salts having reducing activity, such as iron(II) salts, iron(II)ammonium complexes, sulphites, sulfides, dithionites or titanium(III) compounds, or by catalytic reduction with hydrazine or, preferably, hydrogen on nickel, platinum, ruthenium or, preferably palladium catalysts. The reaction is—as usual—carried out in a solvent or dispersant which is inert towards the reactants, preferably water, an alcohol such as methanol, ethanol or isopropanol, or a halogenated hydrocarbon such as dichloromethane, chloroform or tetrachloromethane, or a mixture of these solvents, the reaction temperatures used being between 0° and 100° C., preferably between 20° and 80° C. The catalytic hydrogenation can be carried out with the application of elevated pressures, for example in a Parr apparatus under an excess pressure of up to 10 bar, or, preferably, under atmospheric pressure in a shaking apparatus, generally at 0° to 100° C., preferably at room temperature.

The hydrolysis of the 3-carboxylic esters of the formula I, according to the invention, to give the corresponding 3-carboxylic acids of the formula I as in process variant (f) is preferably carried out under alkaline conditions, where appropriate at elevated temperatures. It is advantageously carried out in a solvent such as water, an ether, ketone or lower monohydric or dihydric alcohol, such as diethyl ether, diisopropyl ether, acetone, methyl ethyl ketone, methyl isobutyl ketone, methanol, ethanol, the various propanols and butanols, the monomethyl or monoethyl ether of ethylene glycol, the two propanediols, but preferably ethylene glycol. The alkaline medium can be set up by, for example, alkali metal hydroxides or carbonates, in particular sodium or potassium hydroxide.

The dehydration of the tertiary alcohols of the formula I, according to the invention, having the structural element of the formula Zb, in which $R^6$ represents a hydroxyl group, to give the unsaturated compounds of the formula I having the structural feature Zc by process variant (g) is likewise advantageously carried out in a solvent such as dilute aqueous mineral acids or in lower monohydric or dihydric alcohols, preferably ethanol, saturated with hydrogen chloride, at temperatures from 0° C. to the boiling point of the particular reaction mixture, preferably at room temperature.

The compounds of the formula I, according to the invention, and their physiologically tolerated salts can, by reason of their pharmacological properties, be used as medicaments, in particular those for the prophylactic and/or curative treatment of atopic respiratory tract disorders, such as allergic rhinitis, allergic asthma and anaphylactic shock, as well as of allergic dermatitis and allergic conjunctivitis, administration of them being either alone, for example in the form of microcapsules, in mixtures with one another, or in combination with suitable auxiliaries, for example vehicles.

Thus the invention also relates to medicaments which contain as active compound, or consist of, at least one compound of the formula I, where appropriate in the form of one of its physiologically tolerated salts, and which represent a genuine enrichment of pharmacy.

The medicaments according to the invention can be administered orally, parenterally, by inhalation, rectally and, where appropriate, transdermally. Examples of suitable solid or liquid pharmaceutical presentations are granules, powders, tablets, coated tablets, (micro)capsules, suppositories, syrups, emulsions, suspensions, ointments, aerosols, drops or injectable solutions in ampoule form, transdermal administration systems as well as products with protracted release of active compound, in whose preparation use is customarily made of auxiliaries such as vehicles, disintegrants, binders, coating and swelling agents, lubricants, flavorings, sweeteners, buffer substances, antioxidants or solubilizers. Examples of auxiliaries which are frequently used and which may be mentioned are magnesium carbonate, tiaanium dioxide, lactose, mannitol and other sugars, talc, lactalbumin, gelatin, starch, vitamins, cellulose and its derivatives, animal and vegetable oils, polyethylene glycols, and solvents such as, for example, sterile water, alcohols, glycerol and other polyhydric alcohols.

The pharmaceutical products are preferably prepared and administered in dosage units, each unit containing as active component a defined dose of a compound of the formula I, where appropiate in the form of one its physiologically tolerated salts. In the case of solid dosage units, such as tablets, suppositories and capsules, this dose can be up to 100 mg, but is preferably 5 to 50 mg, and in the case of injection solutions it is up to 20 mg, preferably 1 to 15 mg, the stated amounts relating to compound I as such.

Suitable for administration by inhalation are aerosols having an active compound content not exceeding 2%, preferably 0.5 to 1%.

The daily doses indicated for the treatment of an adult patient depend on the efficacy of the compounds of the formula I and their salts and are from 5 to 100 mg of active compound, preferably 10 to 60 mg, on oral or rectal administration, and 1 to 40 mg, preferably 3 to 30 mg, on administration intravenously or by inhalation. However, in certain circumstances, higher or lower daily doses may also be advisable. The daily dose can be administered either by a single administratio in the form of a single dosage unit or of several smaller dosage units, or by multiple administration of divided doses at defined intervals.

Finally, in the preparation of the abovementioned pharmaceutical presentations it is also possible for the new compounds of the formula I, and their salts, to be formulated together with other suitable active compounds, for example corticosteroids, brnnchospasmolytics and expectorants.

In the examples which follow, "vacuum" is meant to be that of the water pump. TLC denotes thin-layer chromatography.

EXAMPLES

The structure of the compounds which are described below was proven by elemental analysis and IR and $^1H$ NMR spectra.

(1)
2,6-Dimethyl-3-nitro-4-[(2-{4-diphenylmethyl-1-piperazinyl}ethyl)amino]pyridine 1-oxide trihydrochloride dihydrate 11 g (0.045 mol) of 4-(2-Chloroethylamino)-2,6-dimethyl-3-nitropyridine 1-oxide, 14.8 g (0.059 mol) of 1-diphenylmethylpiperazine and 6 g (0.06 mol) of triethylamlne were heated to boiling in 200 ml of isopropanol for 80 hours in accordance with process variant (a). The solvent mixture was removed by distillation in vacuo, and the residue was partitioned between dichloromethane and water by shaking. The organic phase was evaporated to dryness, the residue was dissolved in ethanol, and ethanolic HCl was added to this solution. After removal of the ethanol by distillation, the trihydrochloride was recrystallized from isopropanol/diisopropyl ether (4:1; vol.):

$C_{26}H_{34}Cl_3N_5O_3 \times 2 H_2O$ (MW: 606.95); melting point 219° C. (decomposition).

Analysis: Calculated: C 51.45, H 5.65, Cl 17.52, N 11.54; Found: C 51.23, H 5.50, Cl 17.79, N 11.28.

It was also possible to prepare the compound from 2,6-dimethyl-3-nitro-4-[(2-{1-piperazinyl}ethyl)amino]-pyridine 1-oxide and bromodiphenylmethane in accordance with process variant (b).

(2)
4-[(2-(4-benzyl-1-piperazinyl)ethyl)amino]-2,6-dimethyl-3-nitropyridine trihydrochloride 13.3 g (0.05 mol) of 4-(2-chloroethylamino)-2,6-dimethyl-3-nitropyridine, 8.56 g (0.075 mole) of 1-formylpiperazine and 10 g (0.1 mol) of triethylamine were heated to boiling in 300 ml of isopropanol for 10 hours. The liquids were removed by distillation in vacuo, and the remaining solid residue was partitioned between dichloromethane an water by shaking. The dichloromethane phase was evaporated, and the residue was recrystallized once from isopropanol and heated to boiling in 6N hydrochloric acid for 2 hours. The solution was then adjusted to pH 7 with 10% strength sodium hydroxide solution, and the water was removed by distillation. The solid residue was purified on silica gel using dichloromethane/methanol (8:2; vol). 4.5 g (0.016 mol) [31.8% of theory] of 2,6-dimethyl-3-nitro-4-[(2-(1-piperazinyl)ethyl)amino]pyridine (melting point of the trihydrochloride 128°–129° C.) were obtained and were heated to reflux with 2.15 g (0.017 mol) of benzyl chloride and 2 g (0.02 mol) of triethylamine in 100 ml of isopropanol for 6 hours in accordance with process variant (b). The solvents were removed by distillation, and the oily residue was extracted by stirring with ethyl acetate, and the mixture was filtered and the filtrate was evaporated to dryness. The residue was taken up in ethanol, ethanolic HCl was added, nd the mixture was evaporated to dryness. The residue from evaporation was recrystallized from isopropanol/diisopropyl ether (4:1; vol.).

Yield: 6.2 g (81% of theory).
$C_{20}H_{30}Cl_3N_5O_2$ (MW: 478.85); melting point 230° C.
Analysis: Calculated: C 50.17, H 6.31, Cl 22.21, N 14.63; Found: C 50.02, H 6.07, Cl 21.93, N 14.51.

It was also possible to prepare the compound from 4-chloro-2,6-dimethyl-3-nitropyridine and 1-(2-aminoethyl)-4-benzylpiperazine in analogy to process variant (d).

(3)
2,6-dimethyl-3-nitro-4-[(2-{4-diphenylmethyl-1-piperazinyl}ethyl)amino]pyridine trihydrochloride In accordance with process variant (c), 10 g (0.08 mol) of 1-(2-chloroethyl)-4-diphenylmethylpiperazine, 13.4 g (0.08 mol) of 4-amino-2,6-dimethyl-3-nitropyridine and 10 g (0.1 mol) of triethylamine were dissolved in 300 ml of isopropanol in a 500 ml round-bottomed flask, and the solution was heated to boiling for 10 hours. It was then cooled to room temperature, and the precipitate was filtered off with suction. The latter was extracted by stirring with ethyl acetate, and the mixture was filtered and the filtrate was evaporated to dryness.

The remaining residue was taken up in ethanol, and ethanolic HCl was added. The solution was evaporated to dryness in vacuo, and the residue was recrystallized from Isopropanol/diisopropyl ethyl (4:1; vol.).

Yield: 18.7 g (39.4% of theory).

$C_{26}H_{34}Cl_3N_5O_2$ (MW: 554.95); melting point 248°–250° C. (decomposition).

Analysis: Calculated C 56.27, H 6.18, Cl 19.17, N 12.62; Found: C 56.03, H 6.17, Cl 19.05, N 12.64.

The compound was also obtained in yields of up to 70% by reaction of 4-(2-chloroethylamino)-2,6-dimethyl-3-nitropyridine with 1-diphenylmethylpiperazine in accordance with process variant (a).

(4)
3-amino-2,6-dimethyl-4-[(2-{4-diphenylmethyl-1-piperazinyl}ethyl)amino]pyridine trihydrochloride dihydrate 13.5 g (0.03 mol) of the base of the nitro compound from Example 3 were dissolved in accordance with process variant (e) in a mixture of 100 ml of methanol and 70 ml of dichloromethane and hydrogenated over 1 g of palladium (10%) on active charcoal in a shaking apparatus with hydrogen at room temperature. When nitro compound was no longer present (TLC check), the catalyst was removed by filtration, and the solvent mixture was removed by distillation. The amorphous residue was partitioned between dichloromethane and water, which had been adjusted to pH 6 with 1N hydrachloric acid, by shaking. The organic phase was evaporated, and the residue was dissolved in ethanol, ethanolic HCl was added, and the resulting precipitate was filtered off with suction and recrystallized from isopropanol.

Yield, 7.2 g (42.8% of theory).

$C_{26}H_{36}Cl_3N_5 \times 2\ H_2O$ (MW: 564.97); melting point 210–212° C.

Analysis: Calculated: C 55.27, H 7.14, Cl 18.83, N 12.40; Found: C 54.98, H 7.02, Cl 18.90, N 12.41.

(5)
2,6-dimethyl-4-[(2-{4-diphenylmethyl-1-piperazinyl}-ethyl)amino]pyridine-3-carboxylic acid trihydrochloride dihydrate A mixture of 8 g (0.017 mol) of ethyl 2,6-dimethyl-4-[(2-{4-diphenylmethyl-1-piperazinyl}ethyl)amino]-pyridine-3-carboxylate (Example 11) and 1.4 g (0.025 mol) of potassium hydroxide were heated at 170° C. in ethylene glycol for 2 hours in accordance with process variant (f). After the solution had been cooled to room temperature it was adjusted to pH 4 with 4N hydrochloric acid. The precipitate which resulted from this was filtered off with suction, washed with water, dried and converted into the hydrochloride with ethanolic HCl. The trihydrochloride dihydrate was precipitated by addition of diisopropyl ether and was recrystallized from isopropanol/diisopropyl ether (4:1; vol).

Yield: 6.5 g (65% of theory).

$C_{27}H_{35}Cl_3N_4O_2 \times 2\ H_2O$ (MW: 589.96); melting point 248°–249° C. (decomposition).

Analysis: Calculated: C 54.97, H 6.66, Cl 18.03, N 9.50; Found: C 54.72, H 6.92, Cl 17.90, N 9.57.

It was also possible to obtain the compound by reaction of 4-(2-chloroethylamino)-2,6-dimethylpyridine-3-carboxylic acid and 1-diphenylmethylpiperazine by process variant a).

(6)
2,6-dimethyl-3-nitro-4-[(2-{4-diphenylmethylene-1-piperidyl}ethyl)amino]pyridine dihydrochloride dihydrate 10 g (0.02 mol) of 4-[(2-{4-hydroxy(diphenyl)methyl-1-piperidyl}ethyl)amino]-2,6-dimethyl-3-nitropyridine dihydrochloride (Example 17) were dissolved in 100 ml of ethanol and saturated HCl gas while cooling in ice, in accordance with process variant (g). This solution was left to stand overnight and then heated to reflux for one hour. The solvent was removed by distillation, and the remaining residue was recrystallized several times from isopropanol/diisopropyl ether (8:2; vol.).

Yield: 3.5 g (31% of theory).

$C_{27}H_{32}Cl_2N_4O_2 \times 2\ H_2O$ (MW: 551.49); melting point: 225°–226° C.

Analysis: Calculated: C 62.91, H 6.26, N 10.87; Found: C 63.07, H 6.24, N 11.12.

The compound can also be obtained by reaction of 4-(2-chloroethylamino)-2,6-dimethyl-3-nitropyridine with 4-diphenylmethylenepiperidine in accordance with process variant (a).

The abovementioned compounds and those prepared in an analogous manner are listed in Table 1 below.

TABLE 1
Compounds of formula I (see claim 1)

| Example | $R^1$ | $R^2$ | $R^3$ | A | Z | n | X | Isolated as | Melting point °C. |
|---|---|---|---|---|---|---|---|---|---|
| 1 | $CH_3$ | $CH_3$ | H | $-C_2H_4-$ | $\begin{array}{c}\diagdown\\ N-CH\\ \diagup\end{array}$ (diphenyl) | 1 | $NO_2$ | 3 HCl 2 $H_2O$ | 219 (Decomp.) |
| 2 | $CH_3$ | $CH_3$ | H | $-C_2H_4-$ | $\begin{array}{c}\diagdown\\ N-CH_2-\\ \diagup\end{array}$ (phenyl) | 0 | $NO_2$ | 3 HCl | 230 |

TABLE 1-continued

Compounds of formula I (see claim 1)

| Example | R¹ | R² | R³ | A | Z | n | X | Isolated as | Melting point °C. |
|---|---|---|---|---|---|---|---|---|---|
| 3 | $CH_3$ | $CH_3$ | H | $-C_2H_4-$ | (CH₃)₂N-CH(Ph)₂ | 0 | $NO_2$ | 3 HCl | 248–250 (Decomp.) |
| 4 | $CH_3$ | $CH_3$ | H | $-C_2H_4-$ | (CH₃)₂N-CH(Ph)₂ | 0 | $NH_2$ | 3 HCl, 2 $H_2O$ | 210–212 |
| 5 | $CH_3$ | $CH_3$ | H | $-C_2H_4-$ | (CH₃)₂N-CH(Ph)₂ | 0 | $CO_2H$ | 3 HCl, 2 $H_2O$ | 248–249 (Decomp.) |
| 6 | $CH_3$ | $CH_3$ | H | $-C_2H_4-$ | (CH₃)₂C=C(Ph)₂ | 0 | $NO_2$ | 2 HCl, 2 $H_2O$ | 225–226 |
| 7 | $CH_3$ | $CH_3$ | H | $-C_3H_6-$ | (CH₃)₂N-CH(Ph)₂ | 0 | $NO_2$ | 3 HCl | 203–204 |
| 8 | $CH_3$ | $CH_3$ | H | $-C_2H_4-$ | (CH₃)₂N-CH₂-CH=CH-Ph | 0 | $NO_2$ | 3 HCl, 2,5 $H_2O$ | 225–226 |
| 9 | $CH_3$ | $CH_3$ | H | $-C_2H_4-$ | (CH₃)₂N-CH(Ph)₂ | 0 | CN | 3 HCl | 225–227 |

TABLE 1-continued
Compounds of formula I (see claim 1)
| Example | R¹ | R² | R³ | A | Z | n | X | Isolated as | Melting point °C. |
|---|---|---|---|---|---|---|---|---|---|
| 10 | CH₃ | CH₃ | H | —C₂H₄— | 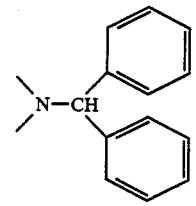 | 1 | CN | 3 HCl 1 H₂O | 219 |
| 11 | CH₃ | CH₃ | H | —C₂H₄— | 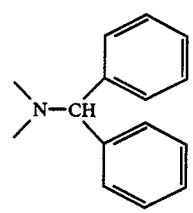 | 0 | CO₂C₂H₅ | 2 HCl 2 H₂O | 220 |
| 12 | C₃H₇ | C₃H₇ | H | —C₂H₄— | 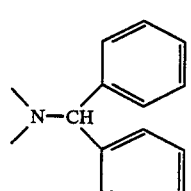 | 0 | NO₂ | 2 HCl | 222 |
| 13 | CH₃ | CH₃ | CH₃ | —C₂H₄— | 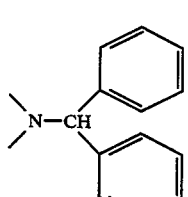 | 0 | NO₂ | 3 HCl 1 H₂O | 214 |
| 14 | CH₃ | CH₃ | H | —C₂H₄— | 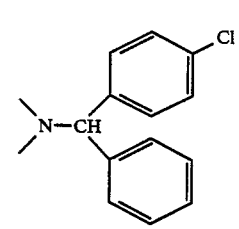 | 0 | NO₂ | 3 HCl 2 H₂O | 210 (Decomp.) |
| 15 | CH₃ | CH₃ | H | —C₂H₄— | 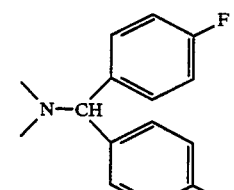 | 0 | NO₂ | 3 HCl 3 H₂O | 197 |
| 16 | CH₃ | CH₃ | H | —C₂H₄— | 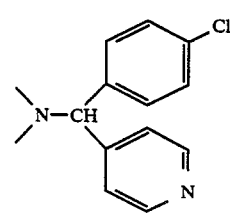 | 0 | NO₂ | 4 HCl | 105 |

TABLE 1-continued

Compounds of formula I (see claim 1)

| Example | $R^1$ | $R^2$ | $R^3$ | A | Z | n | X | Isolated as | Melting point °C. |
|---|---|---|---|---|---|---|---|---|---|
| 17 | $CH_3$ | $CH_3$ | H | $-C_2H_4-$ | $\text{>CH-C(OH)(C}_6\text{H}_5)_2$ | 0 | $NO_2$ | 2 HCl | 217–219 |
| 18 | $CH_3$ | $CH_3$ | H | $-C_2H_4-$ | $\text{>N-CH(4-Cl-C}_6\text{H}_4)(4\text{-F-C}_6\text{H}_4)$ | 0 | $NO_2$ | 3 HCl 2 $H_2O$ | 205 |
| 19 | $CH_3$ | $CH_3$ | H | $-C_2H_4-$ | $\text{>N-CH(C}_6\text{H}_5)(4\text{-OCH}_3\text{-C}_6\text{H}_4)$ | 0 | $NO_2$ | 3 HCl 2 $H_2O$ | 155–158 |
| 20 | $CH_3$ | $CH_3$ | H | $-C_2H_4-$ | $\text{>N-CH(C}_6\text{H}_5)_2$ | 0 | H | 3 HCl | 195–196 |
| 21 | H | H | H | $-C_2H_4-$ | $\text{>N-CH(C}_6\text{H}_5)_2$ | 0 | $NO_2$ | 3 HCl 1 $H_2O$ | 198–199 |
| 22 | H | $CH_3$ | H | $-C_2H_4-$ | $\text{>N-CH(C}_6\text{H}_5)_2$ | 0 | $NO_2$ | 3 HCl | 237 (Decomp.) |
| 23 | $CH_3$ | $CH_3$ | H | $-C_2H_4-$ | $\text{>CH-C(OH)(C}_6\text{H}_5)_2$ | 0 | $CO_2CH_3$ | 3 HCl | 227–228 |

TABLE 1-continued

Compounds of formula I (see claim 1)

| Example | R¹ | R² | R³ | A | Z | n | X | Isolated as | Melting point °C. |
|---|---|---|---|---|---|---|---|---|---|
| 24 | CH₃ | CH₃ | H | —C₂H₄— | 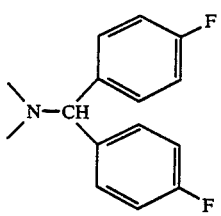 | 0 | CO₂H | 3 HCl 2 H₂O | 161 (Decomp.) |
| 25 | CH₃ | CH₃ | H | —C₂H₄— | 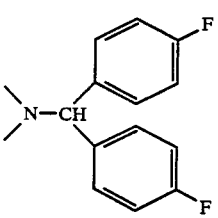 | 0 | NH₂ | 3 HCl 2 H₂O | 190–197 |

Pharmacological Tests and Results

1. Antagonistic action towards the allergy mediators (on anesthetized guinea pigs)

The compounds according to the invention were tested for their inhibitory action on the spasmogenic amines histamine and bradykinin using the experimental design described by H. Konzett and R. Rössler (Arch. Exp. Path. u. Pharmak. 195 (1940), page 71) comparing with the most important representative of the pyridine series which have bronchospasmolytic activity and are state of the aart according to German Offenlegungsschrift No. 2,900,504, i.e. 4-(2,6-dimethyl-3-nitro-4-pyridyl)thiomorpholine hydrochloride (Example 1).

In this method, the inhibition of bronchospasm experimentally induced by intravenous (i.v.) administration of histamine or bradykinin in male guinea pigs under urethane anesthesia (1.25 g/kg i. p.) is investigated. The test substances were administered intravenously in aqueous solution injected in a volume of 1 ml/kg. The criteria used for assessment of the inhibitory action were the $ED_{50}$ values and ranges, these being defined as the doses in mg/kg with which the experimentally induced spasm could be reduced to one half of that in untreated control animals.

2. Inhibition of the release of allergy mediators (protective effect on mast cells)

(a) Passive cutaneous anaphylaxis (PCA) in the rat (PCA test)

Passive cutaneous anaphylaxis is an IgE-mediated allergy of the immediate type (type I). In this model, antibodies bound to mast cells and basophilic granulocytes react with an intravenously administered antigen with release of excessive amount of the allergy mediators. The histamine which is released during this can be visualized by simultaneous application of Evans blue to the shaven flanks of the rats.

Photometric evaluation of the color intensity was used to determine, by means of the percentage inhibition of mediator release compared with untreated control animals, the protective effect on mast cells of the compound according to the invention after oral administration. The abovementioned compound from Example 1 of German Offenlegungsschrift No. 2,900,504 was also included in this investigation and proved to be inactive and thus unsuitable for the therapy of allergic disorders.

(b) Histamine release from isolated rat mast celss induced by calcium ionophore A 23 187

It is possible by use of certain agents, for example calcium ionophore A 23 187 and basic peptides, to stimulate mast cells—similar to the IgE-mediated immune reaction—to excessive release of allergy mediators, of which the histamine which has entered the medium can be quantitatively determined in a relatively straightforward manner.

The protective action on mast cells of the compounds according to the invention was determined via the inhibition of this artificially induced histamine release from rat peritoneal mast cells. For this purpose, $10^4$ cells were suspended in Clicks/RPMI (50:50, vol.; supplied by Serva, Heidelberg) tissue culture medium, incubated with the test substance for 15 minutes, and then treated with calcium ionophore A 23 187 at a concentration of $10^{-6}$ g/ml. The released histamine was determined by high-pressure liquid chromatography (HPLC). The measure used for the inhibitory action was the $IC_{50}$ which represents the molar concentration (mol/l) at which the induced histamine release was decreased to one half that of cells which had not been pretreated with a product. In this context, $IC_{50}$ values above $10^{-5}$ mol/l are regarded as therapeutically irrelevant. According to this, the comparison product of Example 1 of German Offenlegungsschrift No. 2,900,504 proved to be inactive in this test too.

3. Acute toxicity

The $LD_{50}$ values were determined by the standard method of the mortality occurring within 7 days after a single intraperitoneal (i.p.) administration to NMRI mice (NMRI=Naval Medical Research Institute).

The results of these investigations are listed in Tables 2 and 3 which follow.

TABLE 2

Antagonistic action towards the allergy mediators, and acute toxicity

| Compound of Example | Inhibitory action ($ED_{50}$ in mg/kg i.v.) towards | | Acute toxicity $LD_{50}$ (Mouse i.p.) in mg/kg |
|---|---|---|---|
| | histamine | bradykinin | |
| 1 | 0.3–1 | 1–3 | >150 |
| 3 | 0.3 | 0.15 | 300–600 |
| 5 | 1–3 | 3 | 300–600 |
| 6 | 1–3 | 3–6 | 600–1200 |
| 7 | 3 | 3–10 | 150–300 |
| 8 | 3 | 3–10 | 75–150 |
| 9 | 0.3–1 | 3–10 | 300–600 |
| 10 | 0.1–0.3 | 1–3 | 75–150 |
| 13 | 1–3 | 10 | 150–300 |
| 14 | 1–3 | 3–10 | 150–300 |
| 15 | 1–3 | 3–6 | 300–600 |
| 16 | 1 | 1 | 300–600 |
| 17 | 0.3 | 3–10 | 75–150 |
| 21 | 0.02 | 0.03 | 150–300 |
| Compound of Example 1 of German Offenlegungsschrift 2,900,504 | 1.05 | 3.16 | 150–300 |

TABLE 3

Inhibition of release of allergy mediators (Protective action on mast cells)

| Compound of Example | PCA Test | | Inhibitory action in the Ca ionophore test $IC_{50}$ in mol/l |
|---|---|---|---|
| | Oral dose in mg/kg | % inhibition of PCA | |
| 1 | 50 | 91 | $10^{-7}$ |
| 2 | 50 | 67 | $10^{-5}$ |
| 3 | 50 | 85 | $10^{-8}$ |
| | 25 | 61 | |
| | 12.5 | 26 | |
| 4 | 50 | 73 | $5 \cdot 10^{-8}$ |
| 5 | 50 | 91 | $10^{-7}$ |
| 6 | 50 | 91 | n.t.(*) |
| 7 | 50 | 55 | $10^{-8}$ |
| 8 | 50 | 60 | $10^{-7}$ |
| 9 | 50 | 64 | $10^{-8}$ |
| 10 | 50 | 91 | $<10^{-8}$ |
| 12 | 50 | 61 | n.t.(*) |
| 13 | 50 | 68 | $<10^{-8}$ |
| 14 | 50 | 55 | $10^{-6}$ |
| 15 | 50 | 59 | $10^{-7}$ |
| 16 | 50 | 75 | $10^{-7}$ |
| | 25 | 46 | |
| 17 | 50 | 91 | $<10^{-8}$ |
| Compound of Example 1 of German Offenlegungsschrift 2,900,504 | 50 | 13 | $<10^{-4}$ |
| | 25 | 0 | |
| | 12.5 | 0 | |

It emerged from the tests by the Konzett-Rössler model that the compounds of Examples 4 and 5 additionally have a strong anticholinergic action so that these products are also suitable for the treatment of bronchospasms of non-allergic origin.

It was also possible in further special tests to show impressively that the compounds according to the invention have the optimal profile of actions mentioned in the introduction and thus are clearly superior to all the specified products of the state of the art:

The compounds of the formula I and their salts likewise exert a strong inhibitory action on the allergic bronchospasm induced with ovalbumin (1 mg/kg i.v.) in presensitized guinea pigs. Thus, for example, the $ED_{50}$ for the compound of Example 3 is between 0.1 and 0.3 mg/kg i.v.

The efficacy of the compounds according to the invention on administration by inhalation was demonstrated by inhibition of the allergic asthma induced in conscious guinea pigs by histamine. Thus, inhalation of, for example, the compound of Example 3 in the form of an only 0.3% strength aerosol resulted in substantial suppression of the experimentally induced asthma attacks.

The compounds of the formula I and their salts additionally show a pronounced inhibitory action on platelet activating factor (PAF) and the leukotrienes, which are likewise released as spasmogenic mediators from the mast cells during the course of the immediate anaphylactic reaction. It was possible to antagonize the bronchospasm induced in anesthetized rats by administration of PAF by, for example, intravenous administration of the compound of Example 3 with a $ED_{50}$ of 1–3 mg/kg. The said products of the state of the art, such as oxatomide, ketotiphen and terfenadine, have no action in this test. The contractions induced by calcium ionophore A 23 187 in isolated strips of lung and the isolated trachea of guinea pigs were inhibited by, for example, the compound of Example 3 with an $IC_{50}$ of 0.1–0.3 µg/ml. Since calcium ionophore A 23 187 stimulates 5-lipoxygenase and thus promotes the formation of spasmogenic leukotrienes, a possible interpretation of the result of this experiment is that the compounds according to the invention are potent leukotriene inhibitors.

It was finally possible to demonstrate a direct antagonistic action on the leukotrinnes using a test design in which a slowly increasing and long-lasting spasm is induced with leukotriene $D_4$ (10 pg/ml) in the isolated gunea pig trachea, and this spasm can be inhibited by 50% with, for example, the compound of Example 3 in the concentration range 3–6 µg/ml.

It was possible to establish in thorough psychopharmacological investigations that the compounds according to the invention have no sedative side effect. Central sedation is manifested by the reduction in the spontaneous motility of the mouse which is significant after, for example, oral administration of only 1 mg/kg ketotifen, whereas the compounds of the formula I do not affect this parameter even at high oral doses of up to 50 mg/kg.

Plethysmographic investigations on conscious guinea pigs with airway obstruction experimentally induced by inhalation of a 0.3% strength histamine aerosol have shown that the compounds according to the invention very rapidly display their inhibitory action even after oral administration. Thus, for example, the compound of Example 3 reached its maximum effect, with an oral $ED_{50}$ of only 3.15 mg/kg, only 30 minutes after administration, whereas the corresponding figures for the product oxatomide were found to be 25 mg/kg and 90 minutes.

Finally, the compound of Example 3 had no effect, even at high oral doses, on the normal weight gain of rats in a subchronic 14-day experiment. It is evident from this that the compounds of the formula I have no appetite-stimulating action in contrast to many other antihistamines.

FORMULA SHEET

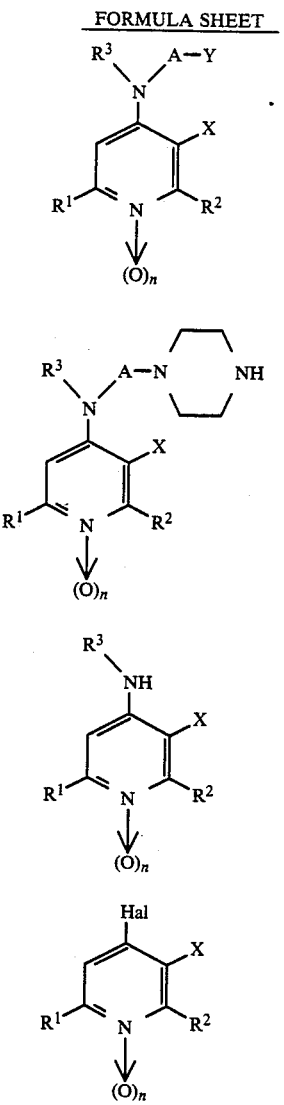

We claim:
1. A pyridine compound of the formula I

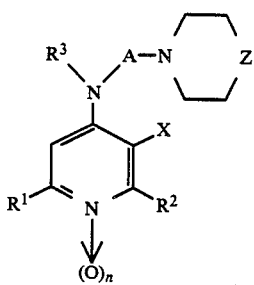

in which
R¹ and R² independently of each other represent hydrogen or alkyl having from 1 to 4 carbon atoms,
R³ represents hydrogen or alkyl having up to 2 carbon atoms and
A represents alkylene having 2 to 4 carbon atoms, n is 0 or 1,
Z is a group of the formula Za, Zb, or Zc

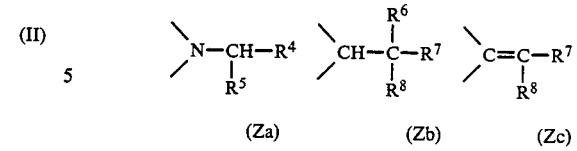

in which either
R⁴ is hydrogen and
R⁵ is phenyl or cinnamyl or
R⁴, R⁵, R⁷ and R⁸ independently of each other are pyridyl, phenyl or phenyl which is substituted by up to 2 equal or different substituents from the group halogen and alkoxy having up to 2 carbon atoms,
R⁶ is hydrogen or hydroxy and
X is hydrogen, a cyano, amino or nitro group or the group —CO—R⁹, in which R⁹ is hydroxy or alkoxy having from 1 to 4 carbon atoms,
and the physiologically tolerable salts of these compounds.

2. A compound according to claim 1 or a salt thereof, characterized by at least one of the features that
(a) the groups R¹ and R² together do not contain more than 6 carbon atoms,
(b) that halogen, if present at a phenyl ring is fluorine, chlorine or bromine and
(c) that A is CH₂—CH₂.

3. A compound according to claim 1 or a salt thereof, characterized by at least one of the features that
(a) the groups R¹ and R² together do not contain more than 2 carbon atoms,
(b) that halogen, if present at a phenyl ring is fluorine or chlorine,
(c) that A is CH₂—CH₂.

4. A compound according to claim 1, or a salt thereof, wherein in formula I both R¹ and R² are methyl, R³ is hydrogen, A is CH₂—CH₂, Z is a group of the formula Za or Zb and X is a cyano or nitro group.

5. A compound according to claim 1, or a salt thereof, wherein in formula I Z is the group of the formula Za in which R⁴ and R⁵ each are phenyl which is unsubstituted or substituted with up to 2 equal or different halogen atoms and wherein R⁴ and R⁵ may be equal or different.

6. A compound or a salt thereof according to claim 5, which is a 3-cyano-2,6-dimethyl-4-[(2-{4-diphenylmethyl-1-piperazinyl}-ethyl)-amino]-pyridine or its 1-oxide.

7. A compound or a salt thereof according to claim 5, which is a 3-nitro-2,6-dimethyl-4-[(2-{4-diphenylmethyl-1-piperazinyl}-ethyl)-amino]-pyridine or its 1-oxide.

8. A pharmaceutical composition comprising an amount effective for use as a pharmaceutical in the allergy therapy of a mammal of at least one compound of the formula I according to claim 1 or a physiologically tolerable salt thereof or a combination thereof.

9. A pharmaceutical composition comprising an amount effective for use as a pharmaceutical in the allergy therapy of a mammal of at least one compound of the formula I according to claim 6 or a physiologically tolerable salt thereof or a combination thereof.

10. A pharmaceutical composition comprising an amount effective for use as a pharmaceutical in the allergy therapy of a mammal of at least one compound of the formula I according to claim 7 or a physiologically tolerable salt thereof or a combination thereof.

11. A pharmaceutical composition according to claim 8 for use in the prophylaxis or treatment or both of allergically conditioned diseases.

12. A pharmaceutical composition according to claim 8 for use in the prophylaxis or treatment or both of allergic rhinitis, allergic asthma, anaphylactic shock, allergic dermatitis or allergic conjunctivitis.

13. A dosage unit form of a pharmaceutical composition according to claim 8 containing an effective amount of at least one compound of the formula I, said compound being present per se or in the form of a physiologically tolerable salt.

14. A dosage unit form as claimed in claim 13 which is in the form of a solid dosage unit which contains up to 100 mg of at least one compound of the formula I, said compound being present per se or in the form of a physiologically tolerable salt.

15. A dosage unit form as claimed in claim 14 which contains from 5 to 50 mg of the compound of the formula I, said compound being present per se or in the form of a physiologically tolerable salt.

16. A dosage unit form as claimed in claim 13 which is present in the form of an injection solution which contains up to 20 mg of the compound of the formula I, said compound being present per se or in the form of a physiologically tolerable salt.

17. A dosage unit form as claimed in claim 16 which contains from 1 to 15 mg of the compound of the formula I, said compound being present per se or in the form of a physiologically tolerable salt.

18. A method of treating a patient suffering from an allergically conditioned disease, wiich comprises administering to a person suffering from such disease an effective amount of a pharmaceutical composition containing as an essential ingredient an effective amount of at least one compound of the formula I as claimed in claim 1 or a physiologically tolerable salt thereof or a combination thereof.

19. A method as claimed in claim 18 of treating a patient suffering from allergic rhinitis, allergic asthma, anaphylactic shock, allergic dermatitis or allergic conjunctivitis.

* * * * *